United States Patent [19]

Napier et al.

[11] 4,003,966

[45] Jan. 18, 1977

[54] SELECTIVE PHOSPHORYLATION PROCESS

[75] Inventors: Roger Paul Napier, Califon, N.J.; Orville L. Chapman, Los Angeles, Calif.

[73] Assignee: Mobil Oil Corporation, New York, N.Y.

[22] Filed: Feb. 10, 1975

[21] Appl. No.: 548,508

[52] U.S. Cl. .............................. 260/971; 260/985
[51] Int. Cl.² ........................................ C07F 9/09
[58] Field of Search .......................... 260/971, 985

[56] References Cited
OTHER PUBLICATIONS

Jacobsen, et al., "J.A.C.S." vol. 77, (1955), pp. 6604–6605.

*Primary Examiner*—Anton H. Sutto
*Attorney, Agent, or Firm*—Charles A. Huggett; Howard M. Flournoy

[57] ABSTRACT

A one step process for the preparation of phosphate esters of phenol comprising reacting phenol with a dimethyl disulfide and a trialkyl phosphite.

9 Claims, No Drawings

SELECTIVE PHOSPHORYLATION PROCESS

BACKGROUND OF THE INVENTION

1. Field of the Invention

This invention is directed to a selective phosphorylation process. More particularly it is directed to a process of phosphorylating phenols comprising reacting an appropriate phenol with dimethyl disulfide and a trialkyl phosphite

2. Description of the Prior Art

It is known that alcohols[1], mercaptans and thiophenols[2] may be phosphorylated by reacting them with, for example, bromotrichloromethane or bromocyanoacetamide[3], and trimethyl phosphite. More recently phenols, oximes and enols have been phosphorylated in similar manner.[4]

The conventional route generally used by commercial producers of phosphates involves a two step reaction, as shown below. A phenol, e.g., phenol is first reacted with sodium carbonate to obtain sodium (phenoxide) which is then reacted in the second step to obtain the phosphate:

[1] A. J. Burn and J. I. G. Cadogan, J. Chem. Soc., 5788 (1963). P. C. Crofts and I. M. Downie, J. Chem. Soc., 2559 (1963).
[2] P. J. Bunyan and J. I. G. Cadogan, J. Chem. Soc., 2953 (1962). L. L. Murdock and T. L. Hopkins, J. Org. Chem., 33, 907 (1968).
[3] T. Hata and T. Mukaiyama, Bull. Chem. Soc. Japan, 35, 1106 (1962).
[4] R. P. Napier and S. T. D. Gough, Org. Preps. and Procedures Int., 3(3), 117 (1971) and British 1309 122.

$$R-OH + Na_2CO_3 \longrightarrow RONa$$

$$RONa + Cl-P\overset{OR}{\underset{\underset{O}{\parallel}}{\diagdown}}OR \longrightarrow RO-P\overset{OR}{\underset{\underset{O}{\parallel}}{\diagdown}}OR$$

See G.M. Kosolapoff "Organophosphorus Compounds", John Wiley & Sons, Inc. New York, New York 1950.

SUMMARY OF THE INVENTION

In accordance with this invention a phosphorylation process is provided in which phosphate esters of phenols are prepared by reaction with dimethyl disulfide and a trialkyl phosphite.

DESCRIPTION OF SPECIFIC EMBODIMENTS

Prior art phosphorylation procedures, previously referred to, did not discern the differences in reactivity between phenols and thiophenols. If a mixture of these reactants were phosphorylated, a corresponding mixture of phosphorylated products would be obtained.

However, we have discovered that the dimethyl disulfide-trialkyl phosphite reagent as embodied in this invention phosphorylates phenols but alkylates thiophenols. Thus, this invention can be used to prepare phenyl dialkylphosphates from phenols, and alkyl phenyl sulfides from thiophenols. This reaction is of particular value in the synthetic of p-methylthiophenyl dialkyl phosphates, e.g., p-mercaptophenol is S-alkylated and O-phosphorylated to P-methylthiophenyl-O,O-dimethyl phosphate with excellent selectivity by the dimethyl disulfide-trialkyl phosphite treatment, i.e. the OH group is phosphorylated in preference to the SH group which is alkylated in preference to the OH group. The present invention, therefore, describes a novel and improved method for phosphorylation of acidic compounds such as phenols.

In accordance with this invention, dimethyl disulfide may be mixed with a trialkyl phosphite, e.g., trimethyl phosphite, to form a reactive complex.

$$CH_3-S-S-CH_3 + P(OCH_3)_3 \longrightarrow CH_3-S-\overset{+}{P}-(OCH_3)_3 \atop {}^-SCH_3$$

Phenol is then added to complete the reaction:

$$CH_3-S-\overset{+}{P}-(OCH_3)_3 \atop {}^-SCH_3 \quad + \quad \underset{}{\text{PhOH}} \longrightarrow$$

$$O^- \quad \overset{+}{P}-(OCH_3)_3 \atop SCH_3 \quad + CH_3SH$$

The complex thus produced reacts to form the final products:

$$O^- \quad \overset{+}{P}-(OCH_3)_3 \atop SCH_3 \longrightarrow O-\overset{O}{\underset{\parallel}{P}}\overset{OCH_3}{\diagdown}OCH_3 + CH_3-S-CH_3$$

Although the initial reactive complex, $$CH_3-S-\overset{+}{P}-(OCH_3)_3 \atop {}^-SCH_3$$

was proposed by H. I. Jacobsen, R. G. Harvey, and E. V. Jensen, J.A.C.S. 77, 6604 (1955), their reported reaction was as detailed below:

$$P(OEt)_3 + Et-S-S-Et \longrightarrow EtS-\overset{+}{P}(OEt)_3 \atop - SEt$$

$$\downarrow \Delta$$

$$EtS-P\overset{OEt}{\underset{\underset{O}{\parallel}}{\diagdown}}OEt \quad +EtSEt$$

Furthermore, Jacobsen et al. did not utilize the complex per se in phosphorylation (of an added reactant) but rather heat decomposed it to form triethyl monothiophosphate. Alternatively, the phenol may be dissolved in the dimethyl disulfide and the trialkyl phosphite then added dropwise to the resulting solution.

This invention is based upon our discovery that phenols can be reacted in the above described manner to change the course of the expected reaction and selectively produce phosphorylated phenols.

This invention therefore specifically provides a process for the selective preparation of O,O-dialkyl phosphates of phenols.

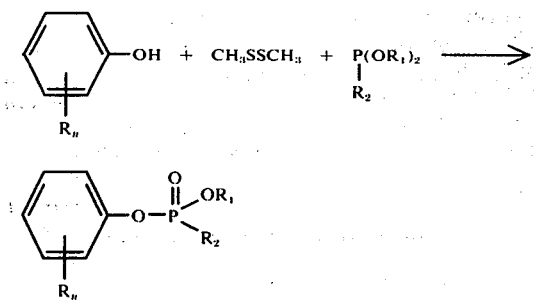

wherein R is selected from the group consisting of H, alkyl of 1–8 carbon atoms, nitro, nitroso, halo, carboxy, carbalkoxy, alkythio, alkylmercapto and haloalkyl of 1–8 carbon atoms, hydroxymethyl, mercaptomethyl, N-hydroxyiminomethyl and $n$ is 1–5; $R_1$ is alkyl of 1–8 carbon atoms and $R_2$ is selected from the group consisting of alkyl of 1–8 carbon atoms, alkoxy, amino and mono or dialkylamino $C_1$–$C_{16}$. Accordingly, the process comprises reacting phenols with the admixture of dimethyl disulfide and trialkyl phosphite each alkyl group thereof having from 1–8 carbon atoms or adding trialkyl phosphite to a mixture of a phenol and dimethyl disulfide.

The reaction temperature may vary within wide limits, i.e. from room temperature to the boiling point of the reactants, however a temperature of from about 30° to about 60° C has proven satisfactory.

In a more specific embodiment of this invention, the phosphorylation process is directed to producing compounds in which R is H or $C_1$–$C_8$ alkylmercapto $R_1$ and $R_2$ are the same or different and are alkyl $C_1$–$C_8$ or more particularly methyl or ethyl.

Suitable trialkyl phosphites include trimethyl phosphite, triethyl phosphite, tributyl phosphite, trinonylphosphite, etc. Generally speaking, trialkyl phosphites having from 1–12 carbon atoms per alkyl group are preferable.

Representative phosphates prepared according to this invention include:

O,O-Diethyl-O-phenyl phosphate,
O,O-Dimethyl-O-phenyl phosphate,
O,O-Diisopropyl-O-phenyl phosphate
O,O-Dibutyl-O-phenyl phosphate,
O,O-Dipentyl-O-phenyl phosphate,
O,O-Diheptyl-O-phenyl phosphate,
O-Ethyl,O-methyl-O-phenyl phosphate,
O,O-Dibutyl-O-(trichlorophenyl) phenylphosphate,
O,O-Dimethyl-O-monochlorophenyl phosphate,
O,O-Diethyl-O-phenyl phosphate,
O,O-Dimethyl-O(p-chlorophenyl) phosphate,
O,O-Diethyl-O-(p-chlorophenyl) phosphate,
O,O-Dimethyl-O-(p-methylphenyl) phosphate,
O,O-Dimethyl-O-(4-benzo (b) thienyl) phosphate,
O,O-Dimethyl-O-(3-methoxyphenyl) phosphate,
O,O-Dimethyl-O-(p-methylthiophenyl) phosphate, etc.

Compounds of this type are useful as insecticides, for example, O,O-Dimethyl-O-(4-methylthiophenyl) phosphate is a known effective insecticide described in U.S. Pat. No. 3,151,022.

SPECIFIC EXAMPLES

EXAMPLE I

Preparation of O,O-Dimethyl-O-Phenyl Phosphate

Trimethyl phosphite (6.2g, 0.05 mole) was mixed with 4.7g (0.05 mole) dimethyl disulfide. Phenol (4.7g 0.05 mole) was added in two equal portions. After each portion was added, an exotherm brought the reaction temperature to 35° C. The reaction mixture was warmed with a heat lamp to 50° C for 5 hours, and methyl mercaptan was evolved. Distillation afforded 6.4g (69% yield) of material with a b.p. of 88°–90° C at 0.1 mm. This material compared spectrally with authentic material prepared in the conventional manner.

EXAMPLE II

Preparation of O,O-Dimethyl-O-(p-methylthiophenyl) Phosphate p-methylthiophenol (7.0g, 0.05 mole) was dissolved in 5.0g (0.053 mole) of dimethyl disulfide. Then 6.2g (0.05 mole) of trimethyl phosphite was added dropwise so as to control the exothermic reaction. After addition was complete, the reaction was warmed to 50° C for 1 hour. Solvents and by-products were removed on a rotating evaporator to afford a quantitative yield of product which exhibited an infrared spectrum which was identical to authentic product prepared in the conventional manner.[5]

[5] See U.S. 3,151,022

EXAMPLE III

Preparation of O,O-Dimethyl-O-(p-methylthiophenyl) Phosphate p-Mercaptophenol (12.6g, 0.10 mole) was dissolved in 20g (0.21 mole) of dimethyl disulfide. Then 24.8g (0.20 mole) of trimethyl phosphite was added dropwise so as to control the exothermic reaction at or below 45° C. The solution was then warmed to 50° C for 1 hour. After cooling to room temperature the solution was distilled to afford 15.1g (69% yield) of product (b.p. 138°–140° C at 0.1 mm). The product was identical to that obtained in the conventional manner.[5]

EXAMPLE IV

Preparation of Methyl Phenyl Sulfide

Benzenethiol (11.0g, 0.10 mole) was dissolved in 9.4g (0.10 mole) of dimethyl disulfide and treated with 12.4g (0.10 mole) of trimethyl phosphite. The reaction solution was washed with aqueous sodium hydroxide and distilled to afford 11.1g (89%) of desired product. The infrared and nmr spectra were identical to that exhibited by authentic material.

EXAMPLE V

Preparation of O,O-Diisopropyl-O-(p-methylthiophenyl) Phosphate p-Methylthiophenol (7.0g, 0.05 mole) was dissolved in 6.0g (0.06 mole) of dimethyl disulfide and treated with 10.4g (0.05 mole) of triisopropyl phosphite and warmed to 50° C for 4 hours. Distillation afforded 7.6g (50% yield) of product with b.p. 136°–138° C at 1.1 mm. Infrared and nmr spectra confirmed the structure.

EXAMPLE VI

Preparation of O,O-Dimethyl-O-(p-chlorophenyl) Phosphate p-chlorophenol (12.9g 0.1 mole) was dissolved in 9.4g (0.10 mole) of dimethyl disulfide and treated with 12.4g (0.10 mole) of trimethyl phosphite. The exothermic reaction was controlled at 45° C by regulation of the rate of phosphite addition. After heating at 50° C for 2 hours, distillation afforded 17.0g (72% yield) of product with b.p. 103°–106 C at 0.07mm. Infrared and nmr specra confrimed the structure.

EXAMPLE VII

Preparation of O,O-Diethyl-O-Phenyl Phosphate

Phenol (9.4g, 0.1 mole) was dissolved in 10g (0.106 mole) of dimethyl disulfide and treated dropwise with 16.6g (0.10 mole) of triethyl phosphite so as to control the exotherm at 40° C. Distillation afforded 15.1g (69% yield) of product with b.p. 101° C at 0.12 mm. The product was identical in all respects to material prepared in the conventional manner.

EXAMPLE VIII

Preparation of O,O-Dimethyl-O-(p-Methylphenyl) Phosphate p-Cresol (10.8g, 0.1 mole) was dissolved in 9.4g (0.1 mole) of dimethyl disulfide and treated dropwise with 12.4g (0.1 mole) of trimethyl phosphite so as to control the exotherm at 40° C. Distillation at 99° C and 0.07 mm afforded 14.4 g (67% yield) of product which exhibited the expected infrared and nmr spectra.

EXAMPLE IX

Preparation of O,O-Dimethyl-O-(4-benzo(b)thienyl) Phosphate

4-Hydroxybenzo(b)thiophene (15g, 0.1 mole) was dissolved in 9.4g (0.1 mole) of dimethyl disulfide and treated with 12.4g (0.1 mole) of trimethyl phosphite at 40° C. Distillation at 145° C and 0.07 mm afforded 17.4g (67% yield) of product which exhibited infrared and nmr spectra consistent with the assigned structure.

EXAMPLE X

Preparation of O,O-Dimethyl-O-(3-methoxyphenyl) Phosphate m-Methoxyphenol(12.4g, 0.1 mole) was dissolved in 9.4g (0.10 mole) of dimethyl disulfide. Then 12.4g (0.10 mole) of tri-methyl phosphite was added dropwise so as to control the exotherm at 40° C. Distillation afforded 16.6g (77% yield) of product which had b.p 119°–121° C at 0.10 mm. The infrared and nmr spectra of the product were consistent with the assigned structure.

The above examples illustrate the novel and unobvious aspects of the claimed process. For example, Examples I and VII illustrate straight-forward phosphorylation of a hydroxy group (phenyl to yield the dialkyl phosphate ester. Examples II and III illustrate that with different starting materials you can still obtain the same final product (process otherwise the same) due to the selectivity of the reagents embodied in the invention toward phosphorylation of hydroxy groups and alkylation of thiol groups; Example IV a straight-forward alkylation of a thio starting material to yield an alkyl phenol sulfide as disclosed supra; Example IV etc also graphically illustrate that a p-mercapto-phenol is selectively S-alkylated and O-phosphorylated via the process embodied by the herein disclosed invention.

Therefore, contrary to the prior art, which taught that a mixture of phosphorylated products would be obtained, the instant process achieves phosphorylation of phenols and alkylation of thiophenols providing for a one-step-process of phosphorylating compounds highly useful in the agricultural chemistry art.

Although the present invention has been particularly described with respect to preferred embodiments, all the disclosed embodiments and modifications apparent to one ordinarily skilled in the art are considered to be within the scope of this invention.

What is claimed is:

1. A process for the selective preparation of O,O-dialkyl phosphates of phenols having the following general formula:

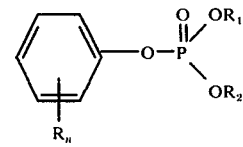

wherein R is selected from the group consisting of H, alkyl of 1–8 carbon atoms, nitro, nitroso, halo, carboxy, carbalkoxy, alkythio, alkylmercapto and haloalkyl of 1–8 carbon atoms, hydroxymethyl, mercaptomethyl, N-hydroxyiminomethyl and $n$ is 1–5; $R_1$ is alkyl of 1–8 carbon atoms; and $R_2$ is selected from the group consisting of alkyl of 1–8 carbon atoms, alkoxy, amino and mono or dialkylamino $C_1$–$C_{16}$ comprising reacting under ambient conditions such phenol with dimethyl disulfide and a trialkyl phosphite each alkyl group thereof having from 1–12 carbon atoms.

2. The process of claim 1 in which R is H or $C_1$–$C_8$ alkylmercapto, $R_1$ and $R_2$ are the same or different and are each alkyl of 1–8 carbon atoms and $n$ is 1.

3. The process of claim 1 in which substantially equimolar amounts of dimethyl disulfide, trialkyl phosphite and phenol are reacted.

4. The process of claim 3 in which $R_1$ and $R_2$ are methyl or ethyl.

5. The process of claim 1 in which the trialkyl phosphite is trimethyl phosphite.

6. The process of claim 1 in which the trialkyl phosphite is triethyl phosphite.

7. The process of claim 1 in which the phosphate prepared is O,O-dimethyl-O-phenol phosphate.

8. The process of claim 1 in which the phosphate prepared is O,O-dimethyl O-(4-methylthiophenyl) phosphate.

9. The process of claim 1 comprising reacting said dimethyl disulfide and said trialkyl phosphite at a temperature of from about 30° to 60° C.

* * * * *

UNITED STATES PATENT AND TRADEMARK OFFICE
CERTIFICATE OF CORRECTION

PATENT NO. : 4,003,966
DATED : January 18, 1977
INVENTOR(S) : ROGER P. NAPIER and ORVILLE L. CHAPMAN It is certified that error appears in the above–identified patent and that said Letters Patent are hereby corrected as shown below:

Column 1, line 15 "bromocyanocacetamide" should be --bromocyanoacetamide--.

Column 1, line 63 "P" should be --p--.

Column 6, line 43 delete "selected from the group consisting of".

Column 6, lines 44 and 45 delete "alkoxy, amino and mono or dialkylamino $C_1$-$C_{16}$".

Column 6, line 46 delete "under ambient conditions" and insert --from about room temperature to the boiling point of the reactants,--.

Column 6, line 48 "12" should be --8--.

Column 6, lines 50 and 51 delete ",$R_1$ and $R_2$ are the same or different and are each alkyl of 1-8 carbon atoms".

Column 6, line 66 after "reacting" insert --said phenol with--.

Signed and Sealed this

Seventh Day of February 1978

[SEAL]

Attest:

RUTH C. MASON
Attesting Officer

LUTRELLE F. PARKER
Acting Commissioner of Patents and Trademarks